(12) United States Patent
Hirayama et al.

(10) Patent No.: US 7,419,673 B2
(45) Date of Patent: Sep. 2, 2008

(54) ANTI-VIRAL AGENTS PREPARED FROM SEA LETTUCE AS RAW MATERIAL

(75) Inventors: Shin Hirayama, Yokohama (JP); Ryohei Ueda, Yokohama (JP); Masashi Miyasaka, Yokohama (JP); Kiyoshi Sugata, Yokohama (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 484 days.

(21) Appl. No.: 11/152,211

(22) Filed: Jun. 15, 2005

(65) Prior Publication Data

US 2005/0232945 A1   Oct. 20, 2005

Related U.S. Application Data

(62) Division of application No. 10/113,287, filed on Apr. 2, 2002, now abandoned.

(30) Foreign Application Priority Data

Apr. 3, 2001 (JP) ............................ 2001-104860

(51) Int. Cl.
*A61K 36/02* (2006.01)
*A23K 1/17* (2006.01)

(52) U.S. Cl. .................. 424/195.17; 424/442

(58) Field of Classification Search ............ 424/195.17, 424/442
See application file for complete search history.

(56) References Cited

FOREIGN PATENT DOCUMENTS

| GB | 1141573 | * | 1/1969 |
| JP | 02001008637 A | | 1/2001 |
| JP | 2001046051 | * | 2/2001 |

OTHER PUBLICATIONS

Caplus Computer Abstract 2002:371897 Hirayama et al "A proposal of valuable production system with coastal seawater remediatin ability by sterile Ulva (Clorophyta" Nippon Kaisui Gakkaishi (2002) 56 (2) 158-165.
Caplus Computer Abstract 2001:875763 Hirayama et al. "Sterile Ulva culture for prduction of useful substances. A proposal of a cysteinolic system applicable for environmental preservation and prod of food and drug materials" Kagaku (2001) 39(11)712-713.
DWIP Derwent No 1990-326-326188 Abstract of JP 02235997 Hasegawa Co Ltd "Prepn of seaweed flavour by exttn with semi-critical or supercritical carbon dioxide in presence of water and/or alcohol" Sep. 18, 1990.
Caplus Computer Abstract 2001:123057 Hirayama et al. "Cysteinolic acid manufacture with sea lettuce" Aug. 1999.
Caplus Computer Abstract 2001:754 018 Hirayama et al "D-Cysteinotic acid derivatives as inhibitors of Fenton reacton and singlet oxygen production" Japanese Patent JP 2001288078 Oct. 2001.
Abstract JPAB of Pub JP02001008637 A Published Jan. 16, 2001.
V. Ivanova, et al., "Isolation of a Polysaccharide with Antiviral Effect from Ulva Lactuca", Preparative Biochemistry, vol. 24, No. 2, 1994, pp. 83-97.
Hari S. Garg, et al., "An Antiviral Sphingosine Derivative From the Green Alga Ulva Fasciata", Tetrahedron Letters, vol. 33, No. 12, 1992, pp. 1641-1644.

* cited by examiner

*Primary Examiner*—Herbert J Lilling
(74) *Attorney, Agent, or Firm*—Oblon, Spivak, McClelland, Maier & Neustadt, P.C.

(57) ABSTRACT

Antiviral agents containing sea lettuce or an organic solvent extraction fraction thereof as an active component, and feeds containing the antiviral agents are disclosed. In addition, a process for preparing the antiviral agents is disclosed.

15 Claims, 2 Drawing Sheets

ANTI-VIRAL AGENTS PREPARED FROM SEA LETTUCE AS RAW MATERIAL

CROSS-REFERENCE TO RELATED APPLICATIONS

This application is a divisional of U.S. application Ser. No. 10/113,287, filed Apr. 2, 2002, which is hereby incorporated by reference.

BACKGROUND OF THE INVENTION

1. Field of the Invention

The present invention relates to use of sea lettuce, a kind of seaweed, and its extract as feed and medicines. In particular, the invention relates to use of the antiviral component contained in the sea lettuce.

2. Description of the Related Art

In fish-farming, there has often seen the overcrowded cultivation that attached great importance to productive efficiency, and because of such the cultivation, various fish diseases to induce death of the cultivated fish have been reported. Among such fish diseases, various medicines such as antibiotics can control fish diseases in the event of onset caused by bacteria and so on, and the control of fish diseases by use of antibiotics has already matured into a particular industrial field in cultivation business.

On viral diseases, damages from various kinds of viral fish diseases has begun to be reported since 1980's. For example, flounder rhabdovirus (HRV: 200 nm overall length, bullet form with an envelope) spread over flounder farms in Hokkaido in the first half of 1980's, and it is reported that 80% of flounder fry died then. In addition, it is said that the amount of damage of salmon family fish by infectious hematopoietic necrosis virus (IHNV: 200 nm overall length, bullet form with an envelope) is estimated to be 2 to 3 billion yen/year, and several 10s billion yen/year in the world. So, many people who involve fish-farming are cautious universally thereon.

However, concerning viral disease countermeasure for the cultivation fish, diagnostic agents and prevention vaccine are being investigated, but the development has not yet advanced so much. For example, vaccine for the iridovirus which was very often reported in cultivating red sea bream and so on was developed in 1999. However, since the vaccine must be injected into each fish, it is not widely used in farms.

On the other hand, sea lettuce is a kind of green alga growing in seawater, and it occurs in mass by the eutrophication which contains much nitrogen and phosphorus in beach and a seawater lake. Therefore, the existence of sea lettuce has been regarded as one of indications to show the eutrophication state of a sea area conventionally. It is assumed that self-purification action by sea lettuce is very important since sea lettuce takes in nitrogen and phosphorus for proliferation. On the other hand, the present ituation is that people rack their brains about disposal of sea lettuce, and its effective utilization is desired. From this point of view, sea lettuce is a practically safe food source which is partly utilized as food, and the basic study aiming at application to feed additives for domestic animal is started, paying attention on nutrition components such as proteins, vitamins, minerals, and so on. However, decisive effective utilization of sea lettuce has not been found yet, and development of the effective usage that is aiming at mass consumption is expected.

The present inventors have investigated in the past for making good use of sea lettuce. As a result, the present inventors have found that D-cysteinolic acid, which is a sulfur-containing amino acid in sea lettuce, reduces internal neutral fat and inhibits the Fentton reaction which generates harmful radicals, and filed already patent applications based on the observations. (Jpn. Pat. Appln. Publication Nos. 2000-202404 and 2000-103724).

However, in terms of effective utilization of sea lettuce, more sufficient analysis and assessment are expected at various points of view about components of sea lettuce.

In view of the circumstances mentioned above, the present invention has been achieved as part of a study to search bioactive components of sea lettuce and to promote effective use thereof.

BRIEF SUMMARY OF THE INVENTION

A first object of the present invention is to provide antiviral agents by use of sea lettuce, namely a material which is already ensured the safety as food.

A second object of the present invention is to provide feeds having antiviral effect by use of sea lettuce.

The present inventors eagerly analyzed and examined about various bioactivity such as antitumor, antibacterial, antimelanin, nerve cell promotion, and antiviral activities on sterile sea lettuce. As a result, it has been found that sea lettuce has antiviral activity, and therefore, the present invention has been established. There has been, so far, no report that sea lettuce and its extract have such physiological activity that inhibits virus infection.

Accordingly, the antiviral agents of the present invention is characterized by containing sea lettuce or an organic solvent extraction fraction thereof.

In addition, the feeds of the present invention is characterized by containing the antiviral agents along with feeding components.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

DETAILED DESCRIPTION OF THE INVENTION

The term "sea lettuce" in the present invention means algae belonging to *Ulva* genus which exist in nature, floating in inlets or the like of the sea. Sterile sea lettuce (*Ulva lactuca*) is preferred as sea lettuce to use with the present invention since it can be easily produced by cultivation through the year.

In the present invention, when an antivirally active component is extracted from sea lettuce, sea lettuce itself (raw algae) or dried algae may be used as raw material. When an antiviral component is extracted from sea lettuce, it is effective to extract from sea lettuce with such amount of organic solvent that is several 10s times by weight per dry weight of the sea lettuce. Further in case of requiring an extract in high purity, high purity extraction can be attained by extracting with several times of water or phosphate buffer (pH 7) by volume per dry weight to extract aqueous fractions, and then, further extracting the resulting residue by adding several 10s times by weight of organic solvent per dry weight of sea lettuce. The organic solvent used here includes, but not limited to, methanol, ethanol, chloroform and the like. The organic solvent may be removed from this extract under a reduced pressure or the like, and the extract can be dissolved in 1% dimethyl sulfoxide (DMSO). Furthermore, the product can be dried by vacuum drying or the like, and it can be saved for a long period in the form of powders.

Organic solvent extraction fraction of the sea lettuce obtained in this way has effective antiviral activity as shown in examples to be described below. Moreover, the sea lettuce itself also showed effective antiviral activity. Therefore, sea lettuce and its organic solvent extraction fraction are useful as antiviral agents.

Furthermore, the present invention provides functional feeds having antiviral activity, in particular. According to one aspect of the invention, there is provided a technology to prevent infection of fish disease viruses by feeding a mixture which is prepared by mixing fine pulverized sea lettuce in 1 mm or less, with facilitated exposition of a lipophilic fraction, and/or the organic solvent extract with any bait composed of known components used conventionally.

Figure 1:
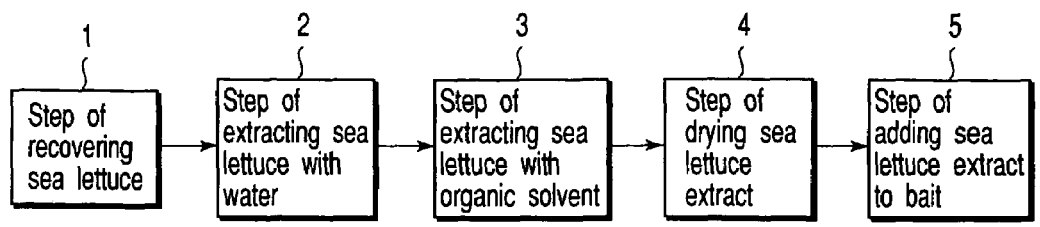
FIG. 1 is a diagrammatic chart showing a step of extracting antiviral components from sea lettuce and a step of processing.

Now, a process for extracting antiviral agents from sea lettuce, and preparing antiviral feeds from the resultant extract will be explained below. As shown in FIG. 1, this process comprises:
  1: a step of collecting sea lettuce;
  2: a step of extracting sea lettuce with water;
  3: a step of extracting sea lettuce with organic solvent;
  4: a step of drying the sea lettuce extract; and
  5: a step of adding the sea lettuce extract to bait.

In Step 1 of collecting sea lettuce, the sea lettuce existing in nature or the sea lettuce produced by cultivation are recovered and collected with a harvest basket. As an apparatus for this purpose, the apparatus as disclosed in Jpn. Pat. Appln. Publication No. 11-066247 by the present inventors can be used.

In Step 2 of extraction from sea lettuce with water, when mud is mixed with sea lettuce, sea lettuce is washed with water, mixed with water in a quantity of several 10s times by weight per dry weight of sea lettuce, crushed by homogenizer and subjected to centrifugal separation or a mesh filtration to obtain the sea lettuce powdery residue.

In Step 3 of extracting sea lettuce with organic solvent, the extraction is performed by mixing the sea lettuce residue with such amount of organic solvent that is several 10s times per dry weight of sea lettuce. Examples of the organic solvent include ethanol, methanol, chloroform and so on, and methanol or ethanol is preferred because of ease on operation.

In Step 4 of drying the sea lettuce extract, it is dried by vacuum freeze dryer or the like. The drying process can make the extract powdery, enabling easy long-term storage. Further, drying of the sea lettuce extract facilitates mixing it with bait. When methanol or chloroform was used for extraction, the drying step is performed after the organic solvent has been eliminated completely under vacuum reduced pressure. However, when less toxic ethanol was used, there is no need of removing the ethanol completely under vacuum reduced pressure, and the extract can be stored as a solution in a small volume of ethanol and the solution can be used in a step of adding the extract to bait as described below.

In Step 5 of adding the sea lettuce extract to bait, the sea lettuce organic solvent extract described above is mixed with formula feeds and fish mince to be fed as a bait. This step of adding is classified in two types, namely a large scale type which is carried out at the place adjacent to a series of sea lettuce extraction steps, and a small scale type which is carried out on the farm spot before the feeding. Even in any case, the organic solvent extract of sea lettuce is desirably mixed with bait at the rate of 0.1 to 2% by weight.

It should be noted that although an organic solvent extracted fraction of sea lettuce is used as an antiviral component in the process of FIG. 1, sea lettuce itself may be used instead. In this case, any one of the sea lettuce from Step 1 of collecting sea lettuce and Step 2 of extracting sea lettuce with water may be used. In any case, appropriate rate of sea lettuce itself to a bait to be mixed is 1 to 20% by weight, preferably 3 to 10% by weight.

EXAMPLES

The present invention will be explained in more detail by way of the following examples.

Example 1

Preparation of Sea Lettuce Extract and Antiviral Activity Test

Sterile sea lettuce (*Ulva lactuca*) collected at a sea area in Yokohama Sea Park was used for this experiment. Note that, a deposition application of the sea lettuce used here was filed as sterile sea lettuce MHI-ATRC-1 strain in National Institute of Bioscience and Human-Technology, Agency of Industrial Science and Technology, but the deposition of this strain was rejected because it is a green alga not applicable to deposition.

Phosphate buffer (pH 7) was added to 10 g of sea lettuce as dry weight, and the mixture was crushed. Extraction in water was performed to give aqueous solution, and further extraction from the residue with organic solvent was performed. The extracted component was dried and weighed. As a result, the component extracted with phosphate buffer weighed 480 mg, the component with chloroform weighed 1000 mg, the component with methanol weighed 1440 mg, and the component with ethanol weighed 1520 mg. In case of ethanol and methanol both of which are preferable because of easy use, almost same weight of crude extract was obtained. Each extracted fraction was dissolved in 1% dimethyl sulfoxide, and this solution was used for assessing antiviral activity.

Antiviral activity of the sea lettuce extract was assessed using two kinds of fish disease viruses: flounder rhabdovirus (HRV8401-H strain/host: EPC cell derived from carp) and infectious hematopoietic necrosis virus of salmon family fish (IHNVChAb strain/host: CHSE-214 cell derived from king salmon embryo). After contacting the sea lettuce extract with virus solution for one hour, a virus was inoculated into various host cells. After inoculation, the virus was cultured for 7 days on dish, and a number of plaques (a group of cells which was dissolved by means of viral infection appeared in the shape of a pin hole) which appear by the cultivation was counted. Percentage reduction was measured by assuming the number of plaques without adding the sea lettuce extract as 100.

Figure 2:
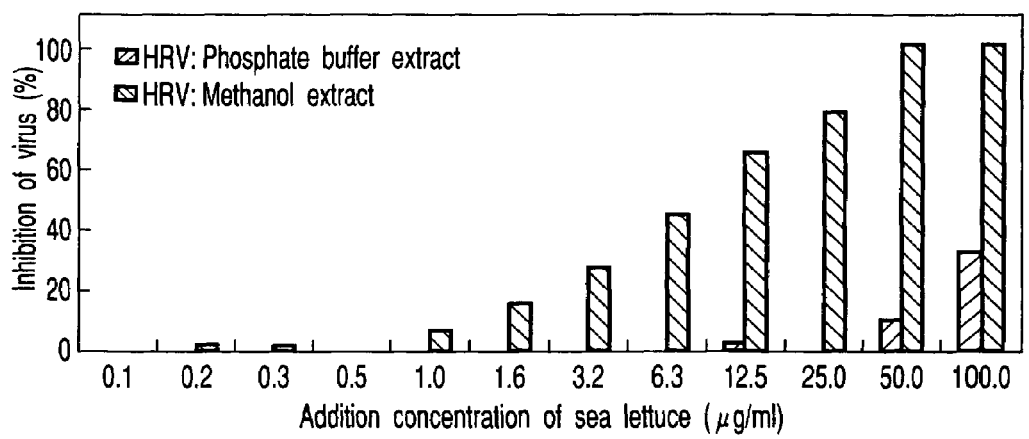
FIG. 2 is a diagrammatic chart showing an inhibitory effect of the sea lettuce extract against flounder rhabdovirus.
Figure 3:
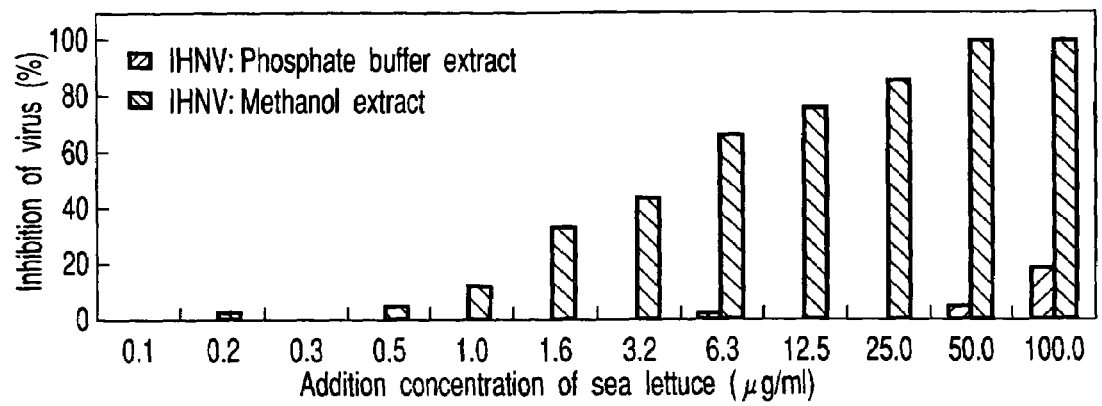
FIG. 3 is a diagrammatic chart showing an inhibitory effect of the sea lettuce extract against salmon family fish infectious hematopoietic necrosis virus.

Virus infection inhibitory effect of the methanol extract and phosphate buffer extract of sea lettuce was examined by using the two kinds of viruses. As shown in FIGS. 2 and 3, eventually the methanol extract inhibited infection of two kinds of viruses (IHNV; HRV) depending upon the concentration of the extract. Plaque was completely (100%) inhibited at a concentration of not less than 50 μg/ml of the methanol extract. As shown in FIGS. 2 and 3, the inhibition of the plaque formation was hardly seen in the phosphate buffer extract of sea lettuce.

Figure 4:
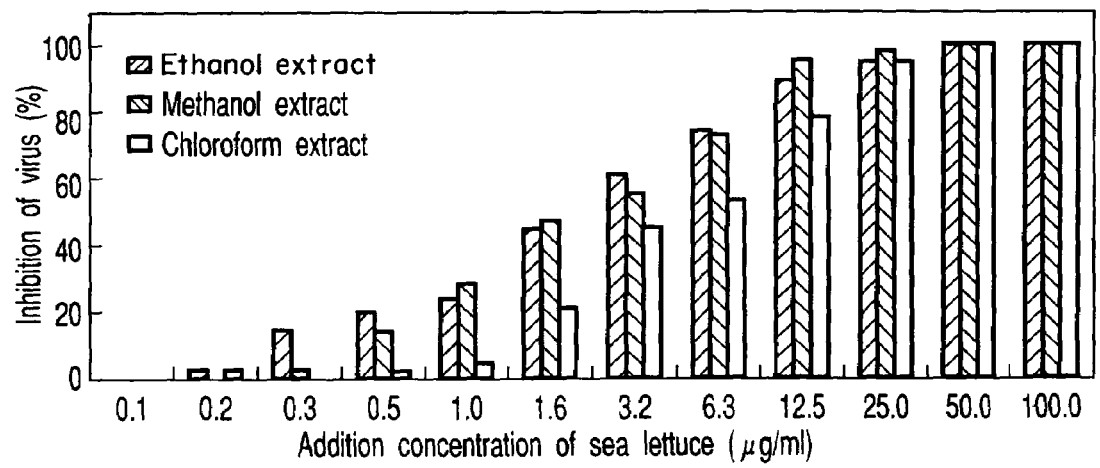
FIG. 4 is a diagrammatic chart showing an inhibitory effect of various sea lettuce extracts against salmon family fish infectious hematopoietic necrosis virus.

Furthermore, antiviral activity of the ethanol extract and chloroform extract were compared on IHNV which was inhibited by the methanol extract. As a result, comparable virus inhibitory effect was observed in three kinds of organic solvent extracts (methanol, ethanol, and chloroform) as shown in FIG. 4. It can be considered that the component having this antiviral activity be a lipophilic substance. Although the mechanism of action is not clear, but it is considered that, because the active component of the organic solvent extract of sea lettuce is lipophilic, the active component exhibits the antiviral effect by acting on the envelope portions of virus (membrane composed of fat and protein).

Example 2

Addition of Sea Lettuce to Bait and Antiviral Activity

Addition of sea lettuce to bait was performed by adding fine powder of dry sea lettuce to the conventional formula feeds mixed with fish oil, vegetable oil, or the like. Addition concentration of solid was 10% by weight. The addition of the sea lettuce extract was performed by adding fine powder of the extract to the formula feeds mixed with fish oil, vegetable oil or the like. The solid was added with 2% concentration by weight. Both of thus obtained two mixed feeds can keep their shape even in water, and a cultured fish (flounder) was able to be easily ingest.

In order to confirm antiviral activity of sea lettuce, viral tolerance of the flounder adult fish treated with sea lettuce or its methanol extract was examined. After feeding bait containing 10% by weight of fine powder of sea lettuce or 2% by weight of its methanol extract to each group of 100 flounders infected with HRV virus, and they were bred for 5 weeks, the survival rate thereof was examined. The result is shown in Table 1. As shown in Table 1, the survival rate of the group treated with normal bait markedly lowered to 59%. On the other hand, the group treated with sea lettuce powder showed 94% of survival rate, and the group treated with the methanol extract showed 96% of survival rate.

TABLE 1

| | Survival rate of flounder | | |
| --- | --- | --- | --- |
| | | Feeding conditions | |
| Conditions for virus inoculation | No addition | 10% of sea lettuce added | 2% of sea lettuce extract added |
| Virus inoculated | 59% | 94% | 96% |
| No virus inoculated | 95% | 96% | 97% |

In addition, the survival rate in the blank test in which the flounder without infection of HRV virus was cultured is shown below as follows: 95% in case of no sea lettuce added; 96% in case of powdery sea. lettuce added; and 97% in case of methanol extract of sea lettuce added. Thus, this had no influence on the antiviral activity described above.

From the result described above, resistance against viral disease can be conferred to adult fish, namely reduction of the death rate by viral diseases can be achieved by feeding sea lettuce or an organic solvent extract thereof which contains antiviral components.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for preventing or treating a viral disease in a fish comprising administering to a fish in need thereof an amount of a feed or bait comprising an organic solvent extract of sea lettuce of the genus *Ulva* effective to prevent or treat said viral disease.

2. The method of claim 1, wherein said feed or bait comprises an organic solvent extract of sea lettuce in an amount ranging from 0.1 to 2% by weight.

3. The method of claim 1, wherein said feed or bait comprises an organic solvent extract of sea lettuce as raw algae.

4. The method of claim 1, wherein said feed or bait comprises an organic solvent extract of dried sea lettuce.

5. The method of claim 1, wherein said feed or bait comprises a methanol extract of sea lettuce.

6. The method of claim 1, wherein said feed or bait comprises an ethanol extract of sea lettuce.

7. The method of claim 1, wherein said feed or bait comprises a chloroform extract of sea lettuce.

8. The method of claim 1, wherein said feed or bait comprises a formula feed to which the sea lettuce extract is added.

9. The method of claim 1, wherein said feed or bait comprises fish mince to which the sea lettuce extract is added.

10. The method of claim 1, wherein said feed or bait inhibits the growth of flounder rhabdovirus.

11. The method of claim 1, wherein said feed or bait inhibits the growth of infectious hematopoictic necrosis virus.

12. The method of claim 1, wherein said fish is a flounder.

13. The method of claim 1, wherein said fish is a member of the salmon fish family.

14. The method of claim 1, wherein the feed or bait containing the organic solvent extract of sea lettuce is obtained by:
   crushing sea lettuce of the genus *Ulva* in water and recovering the sea lettuce residue,
   extracting the sea lettuce residue with an organic solvent, and
   recovering the organic solvent extracted fraction, optionally, drying said organic solvent extracted fraction, and adding said fraction to a feed or bait.

15. The method of claim 1, wherein the feed or bait containing the organic solvent extract of sea lettuce is obtained by:
   extracting sea lettuce with water for removing water-soluble components from the collected sea lettuce;
   extracting a lipophilic fraction from the residue obtained by extracting with water; and
   drying the lipophilic fraction obtained from extracting with organic solvent, and
   adding said dried lipophylic fraction to a feed or bait.

* * * * *